May 20, 1941. J. DE VINK Plant Pat. 466
ROSE PLANT
Filed Nov. 8, 1940
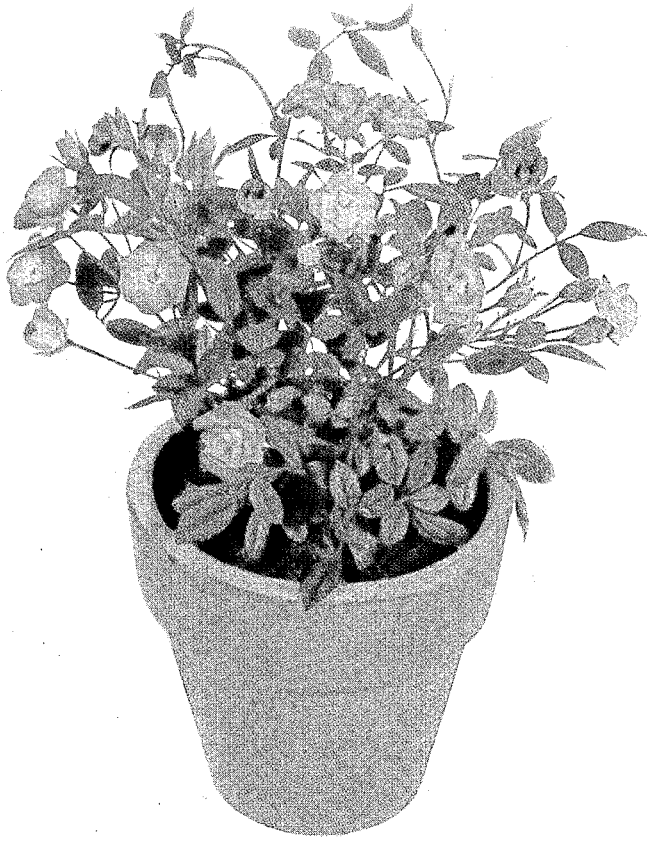
INVENTOR
John de Vink
BY Robt. & Robt.
ATTORNEYS Patented May 20, 1941

Plant Pat. 466

UNITED STATES PATENT OFFICE

466

ROSE PLANT

John de Vink, Boskoop, Netherlands, assignor to
The Conard-Pyle Company, West Grove, Pa.

Application November 8, 1940, Serial No. 364,928

1 Claim. (Cl. 47—61)

The present invention relates to a new and distinct variety of rose plant, of the type known as dwarf or miniature roses, and as such it differs entirely from any other rose now known to commerce, including those of the *Indica mimina* species.

It is not only unique with respect to its size but also in respect to its fern-like foliage, with narrow-pointed leaves, and the symmetry of its growth.

In addition to the foregoing, distinctiveness is found in the quality of the diminutive flower borne by the plant, that is, its perfection in form and the particular color thereof, as yet not even approached by any of the miniature roses of this general type or group.

Asexual reproduction shows the dominant characteristics herein set forth to be established.

The following is a detailed description of this new rose, the color terminology employed therein being in accord with Ridgway's Color Standard:

Type:
Hardy; dwarf; greenhouse and outdoors; seedling; for cut flowers and garden decoration.

Class:
Lawranceana.

Parentage:
*Seed parent.*—Ellen Poulsen.
*Pollen parent.*—Tom Thumb.

Propagation:
Holds its distinguishing characteristics through succeeding propagations by cuttings and budding.

*Flower*

Locality where grown:
West Grove, Pennsylvania.

Flowers borne:
Several to stem; in regular clusters; on strong, short stems.

Quantity of bloom:
Abundant, outdoors and in greenhouse.

Continuity:
Continuous.

Fragrance:
Slight; tea.

Bud:
*Peduncle.*—Short; slender; erect; Lettuce Green, Plate V; smooth; no hairs.
*Before calyx breaks.*—Size—small, ¼ inch. Form—ovoid with a conspicuous neck, with foliaceous appendages on the surface of the bud, with bristle like foliaceous parts extending beyond the tip of the bud equal to one-half or more of its length.
*As calyx breaks.*—Color—Deep Rose Pink, Plate XII.
*As first petal opens.*—Size—very small. Form—ovoid. Color—Outside—Deep Rose Pink, Plate XII. Inside—Rose-Red, Plate XII. Opening—opens up well.

Bloom:
*Size, when fully open.*—Very small, ½ to ⅝ inch.
*Petalage.*—Double, usually with no stamens showing; from twenty to twenty-five arranged regularly.
*Form.*—Full at first; becoming flat; petals remaining at first loosely rolled outward; becoming later, at maturity, very loosely rolled outward.

Petals:
Soft, with inside satiny and outside shiny.
*Shape.*—Outside—oval with apex flat, with no notches. Intermediate—oval with apex flat, with no notches. Inside—obovate with apex flat, with no notches.

This description of a newly opened flower was made from a rose grown in a greenhouse, in August, 1940, at West Grove, Pennsylvania:

*Color.*—Outside petal — Outside surface—Deep Rose Pink, Plate XII; white base. Inside surface—Rose Red, Plate XII; white base. Intermediate petal—Outside surface—Deep Rose Pink, Plate XII; white base. Inside surface—Rose Red, Plate XII; white base. Inner petal—Outside surface—Deep Rose Pink, Plate VII; white base. Inside surface—Rose Red, Plate XII; white base.

This description was made from a rose that was open for three days in a greenhouse, in August, 1940, at West Grove, Pennsylvania:

*Color.*—Outside petal — Outside surface—Rose Pink, Plate XII; white base. Inside surface—Deep Rose Pink, Plate XII; white base. Inside petal—Outside surface—Rose Pink, Plate XII; white base. Inside surface—Deep Rose Pink, Plate XII; white base.

*General color effect.*—Newly opened flower—Rose Red, Plate XII. Three days open—Deep Rose Pink, Plate XII.

*Behavior.*—Persist; fading Rose Pink, Plate XII.

*Flower longevity.*—Cut roses grown in greenhouse kept at living room temperature 4 to 6 days in August.

*Reproductive organs*

*Stamens.*—Very few.

*Filaments.*—Short; Raw Sienna, Plate III, with anthers.

*Anthers.*—Small; Deep Chrome, Plate III.

*Pollen.*—None available.

*Pistils.*—Very few.

*Styles.*—Short; very thin; bunched.

*Stigma.*—Pale Orange Yellow, Plate III.

*Ovaries.*—All enclosed in calyx.

*Hips.*—No record.

*Sepals.*—Permanent; moderately long; spear-shaped, recurved.

*Plant*

Foliage:

*Leaves.*—Compound of 3, 5, 7, leaflets; abundant; very small; moderately soft.

*Leaflets.*—Lanceolate with apex murcronate; base obtuse; margin dentate.

*Color.* — Mature — Upper surface — Forest Green, Plate XVII. Under surface—Roman Green, Plate XVI. Young—Upper surface—Oil Green, Plate V. Under surface—Bronzy Grass Green, Plate VI.

*Rachis (the supporting stem of the compound leaf).*—Light. Upper side—smooth, grooved. Under side—smooth.

*Stipules.*—Short; narrow; with short points, turning out at an angle of less than 45°.

*Disease.*—Subject to blackspot.

Growth:

*Habit.* — Dwarf; bushy; upright; much branched.

*Growth.*—Stumpy.

*Canes.*—Light.

*Main stems.*—Oil Green, Plate V. Thorns—few; short; straight; with narrow base. Prickles—none. Hairs—none.

*Branches.*—Thorns, prickles and hairs—none.

*New shoots.*—Bronzy Grass Green, Plate VI. Thorns, prickles and hairs—none.

I claim:

A new and distinct variety of rose plant of the *Indica mimina* species, characterized as to novelty by symmetrical habit of growth and diminutive size, its fern-like narrow-pointed leaves, and the perfect form and novel color of the flowers, substantially as shown and described.

JOHN DE VINK.